United States Patent [19]

Schmedemann et al.

[11] 4,050,551
[45] Sept. 27, 1977

[54] DEVICE FOR BRAKING A COUNTERWEIGHT IN AN X-RAY EXAMINING APPARATUS

[75] Inventors: Walter Schmedemann; Wolfgang Hecker, both of Hamburg, Germany

[73] Assignee: U.S. Philips Corporation, New York, N.Y.

[21] Appl. No.: 604,242

[22] Filed: Aug. 13, 1975

[30] Foreign Application Priority Data

Aug. 28, 1974 Germany ............................. 2441265

[51] Int. Cl.² .............................................. B60T 8/02
[52] U.S. Cl. .................................. 188/181 C; 303/95;
250/439 R; 250/449; 361/237
[58] Field of Search ............ 73/507; 180/82 R, 105 E;
187/29 R; 188/181 C; 235/150.2; 246/182 R,
182 B, 182 C; 303/20, 21, 95; 317/5, 19; 318/60,
63, 86, 204, 304; 250/439, 444–450; 340/263;
324/160–161

[56] References Cited
U.S. PATENT DOCUMENTS

| 3,070,185 | 12/1962 | Fales ................................. 180/105 E |
| 3,450,943 | 6/1969 | Burke et al. ............................. 317/5 |
| 3,601,227 | 8/1971 | Burch ................................. 187/29 R |
| 3,808,427 | 4/1974 | Malon et al. ................. 246/182 C X |
| 3,832,010 | 8/1974 | Grosseau ..................... 303/21 CF X |
| 3,866,048 | 2/1975 | Gieschen et al. .................... 250/449 |
| 3,916,203 | 10/1975 | Norgren ............................... 250/439 |

FOREIGN PATENT DOCUMENTS 1,048,668  1/1959  Germany ............................ 250/439

Primary Examiner—Stephen G. Kunin
Attorney, Agent, or Firm—Frank R. Trifari

[57] ABSTRACT

In X-ray examining apparatus in which a compression counterweight is uncoupled in the vertical position, a problem exists in that, when the examining apparatus is turned over, the compression counterweight is coupled to the X-ray image section with a jolt. So as to avoid this jolt, pneumatic damping devices are known which, however, are very voluminous. According to the invention, a simple and efficient device for the damped coupling comprises a control circuit which brakes the counterweight when it exceeds a given speed.

1 Claim, 5 Drawing Figures

DEVICE FOR BRAKING A COUNTERWEIGHT IN AN X-RAY EXAMINING APPARATUS

The invention relates to a device for braking a counterweight in an X-ray examining apparatus, wherein the counterweight serves to compensate for the weight of a section of the apparatus, notably an X-ray image section, and can be uncoupled from this section in the perpendicular position of the X-ray examining apparatus.

In X-ray examining apparatus, the weight of a section to be moved is generally compensated for by a counterweight which is connected, via a cord or the like, to the section such that, when the section moves, the counterweight moves in the opposite direction. The operator then has to accelerate twice the mass of the section, but does not have to overcome the force of gravity acting on the section. This double mass is to be accelerated by the operator also when the X-ray examining apparatus has been moved into a position in which the section to be moved completes a trajectory perpendicular to the direction of the force of gravity. In this position of the X-ray examining apparatus, the counterweight per se is superfluous; therefore, X-ray examining apparatus are known wherein in this position the counterweight is uncoupled from the section to be moved, so that during movement of the section the counterweight does not move.

For example, German Auslegeschrift 1,048,668 describes an X-ray examining apparatus wherein the counterweight is uncoupled from the examining apparatus for the compression movement of the X-ray image section in the perpendicular position. To this end, a small force, wich is produced, for example, by means of a spring or an additional weight, acts on the counterweight, so that this weight is moved into an end position near the X-ray image section. When the X-ray examining apparatus is turned over, the counterweight rolls down at an increasing speed, due to the increasing slope of the guide track, until the cords whereby the counterweight is connected to the image section are taut. The X-ray image section, usually locked by means of a brake during the turning over of the X-ray examining apparatus, is then jolted, the jolt being larger as the X-ray image section is further removed from the bearing plate of the X-ray examining apparatus at the instant of turning over.

In order to avoid excessive jolts, practical apparatus of this kind include a damping piston which is mounted on the image section and which damps the jolt occurring when the counterweight is coupled after the turning over of the X-ray examining apparatus. However, the damping piston has a plurality of drawbacks. For example, obstruction of the sliding movement of the image section by the damping piston when the apparatus is in the vertical positions cannot be completely avoided, so that an additional force must be delivered for the movement of the image section. Due to the provision of the damping cylinder, the weight of the image section is increased; consequently, the counterweight must also be heavier. The influencing of the movement of the counterweight by the damping piston is optimum only for a given mass of a counterweight or the image section and for a given turn-over speed of the X-ray examining apparatus. If a dfferent turn-over speed is chosen, there will also be speed of the counterweight and kinetic energy to be cancelled by the damping piston. The same is applicable when an image section having a different weight and hence other counterweights is used.

The invention has for its object to provide a device for braking a counterweight of an X-ray examining apparatus which does not impede the movement of the counterweight and the image section, except when the counterweight is coupled, while during the movement of the image section in the compression direction no other components need be moved, jolt-free coupling of the counterweight being possible upon turning over, independent of the turn-over speed and the mass of the image section used.

To this end, the invention is characterized in that there is provided a speed detector which is adapted to generate a signal which is dependent of the speed of the counterweight and which is applied to a control circuit which actuates a brake for braking the counterweight when the amplitude of the signal exceeds a predetermined value.

After the turning over of the X-ray examining apparatus, the counterweight then initially rolls down without being braked, until its speed assumes a value such that the signal generated by the speed detector exceeds a predetermined value. At this instant the brakes are actuated to ensure that the counterweight substantially maintains the speedreached. This speed or the signal amplitude at which the brakes are actuated is chosen such that the kinetic energy of the counterweight at the instant of braking is too small to produce a noticeable jolt.

The invention will be described in detail hereinafter with reference to one embodiment according to the invention which is shown in the accompanying drawing.

Figure 1:
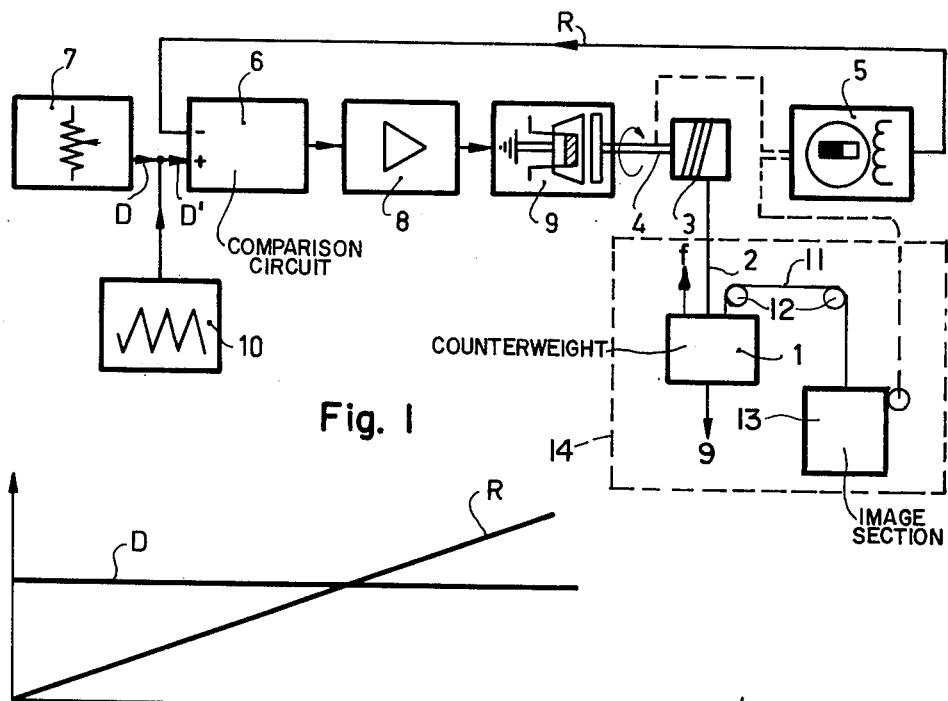
FIG. 1 shows a block diagram of a device according to the invention.

The reference 1 in FIG. 1 denotes the counterweight. Counterweight 1 is connected by a cord 11 over guide rollers 12 to the image section 13 of X-ray examining apparatus 14. When the X-ray examining apparatus is rotated so that gravity g no longer keeps cord 11 taut, counterweight 1 is brought to and retained at the extreme upper position shown by a small force f from a spring or small weight (not shown). The counterweight 1 is thus uncoupled from the image section 13 until the examining apparatus is rotated back so that gravity again makes cord 11 taut. The counterweight is secured to a wire 2 which is guided about a drum or guide roller 3 which starts to rotate when the counterweight 1 moves. The number of revolutions of the drum 3, and hence also the speed of the counterweight 1, is measured on the shaft 4 of the drum by means of a tachometer 5. For the tachometer use can be made, for example, of a synchronous motor, the output voltage of which is rectified and smoothed. The signal supplied by the tachometer 5 is applied to a comparison circuit 6 and is compared with an adjusted value which can be adjusted by means of a potentiometer of an adjusted value generator 7. If the adjusted value exceeds the actual value supplied by the tachometer 5, an amplifier 8, driven by the comparison circuit 6, is blocked, so that the counterweight can continue its travel without being braked. However, if the actual value exceeds the adjusted value, an electromagnetic brake 9 is actuated, via the amplifier 8, which acts on the shaft 4 of the drum 3 and hence on the counterweight.

Figure 2A:
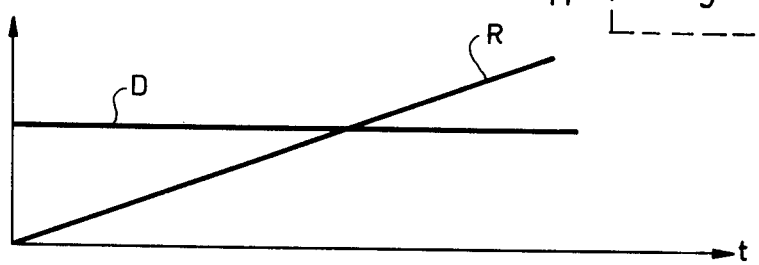
FIGS. 2a to 2d show diagrams of the variation of the adjusted value, of the signal generated by the speed detector, and of the actuation of the brake.
Figure 2B:
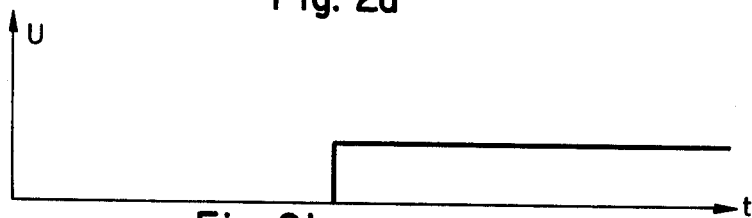

FIG. 2a shows the variation in time of the adjusted value D and the variation in time of the actual value R; the actual value is shown as if the counterweight continues its travel without being braked. FIG. 2b shows the associated variation U of the actuation of the electromagnetic brake as a function of the time. It appears that the brake is actuated only when the actual value R reaches the adjusted value D. The brake remains actuated until the actual value decreases below the adjusted value again. Experiments have revealed that this abrupt braking is accompanied by vibrations of 3 Hz to 5 Hz. These vibrations are caused in that on the one hand the counterweight is comparatively elastically coupled to the brake and the tachometer via wires, while on the other hand the increase of the braking force is very abrupt.

Figure 2C:
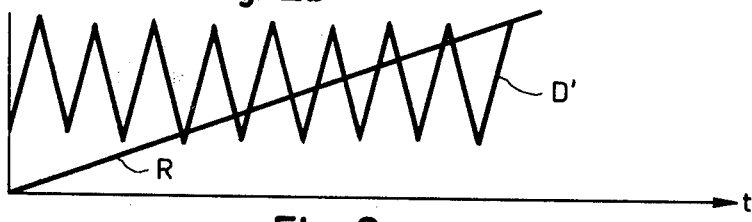
Figure 2D:
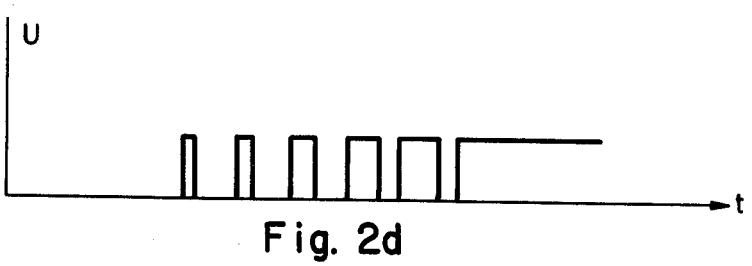

In order to achieve low-vibration braking of the counterweight, moreover, a delta generator 10 is provided, the output voltage of which is superposed on the adjusted value D (or on the actual value R, or on the difference between adjusted value and actual value). The frequency of the generated delta voltage is chosen to be such that on the one hand the described vibrations are suppressed and on the other hand the control of the (inductively operating) electromagnetic brake is not problematic; in practice a value of a few kHz was found to be satisfactory. The amplitude of the delta voltage should be in the order of magnitude of the adjusted value; suitable values are obtained when the amplitude of the delta voltage relates to the adjusted value approximately as 0.7 : 1. The effect of this step will be described with reference to FIGS. 2c and 2d. When the delta voltage is superposed on the adjusted value, the actual value R of the speed is no longer compared with a constant signal D, but with a signal D' which fluctuates about the adjusted value in accordance with the delta voltage. Consequently, the actual value already becomes larger than the lower peak of the superimposed delta voltage D' soon after the turning over of the X-ray examining apparatus. As a result the amplifier 8 is driven for a brief period of time comparatively early already, and the electromagnetic brake 9 is actuated accordingly. The larger the actual value R, the longer the actuation of the magnetic brake 9 (see FIG. 2d). Due to the inertia of the magnetic brake 9, the pulses whose frequency corresponds to the delta voltage and whose duration is dependent of the actual value R are integrated, so that the effective actuation of the magnetic brake increases in accordance with the actual value of the speed.

The described control circuit thus behaves as an analog control amplifier, but in comparison therewith it offers the advantage that the power loss in the transistors of the amplifier 8 controlling the electromagnetic brake 9 is small, because the transistors are either turned off or turned on. Moreover, the device is not susceptible to disturbing effects, such as friction of the mechanical elements and the dead time introduced by the air gap and the inductance of the brake which are practically eliminated by the pulse-wise actuation of the brake. The braking action commences sooner and increases less steeply as the amplitude of the delta voltage is higher in comparison with the adjusted value. The tendency to vibrate is also reduced to an equal degree. The braking behaviour of the device can be adapted to individual requirements by changing the adjusted value and/or the superimposed delta voltage.

If the image section 11 (and hence also the counterweight) is moved comparatively quickly after the coupling of the counterweight to the image section, the speed thereof may exceed the adjusted value, after which the movement is braked. This can be avoided by deactivating the control circuit or a part thereof, for example, the amplifier 8, after the coupling. A criterion for the automatic switching off of the control circuit or the amplifier consists in the fact whether or not the counterweight starts to move when the image section has been locked (the image section is always locked during turning over). However, such a step is not necessary if, instead of the absolute speed of the counterweight, the tachometer 5 measures the relative speed of components (guide rollers and the like) connected to the counterweight (guide roller 3) the image section (guide roller 15), which travel at the same speed when the counterweight is coupled, while when the counterweight is uncoupled, the part connected to the image section is stationary and the part connected to the counterweight is in motion.

what is claimed is:

1. X-ray apparatus comprising:
an image section;
a counterweight for compensating for the weight of said image section, said counterweight being uncouplable from said image section when said image section is in an orientation not requiring weight compensation;
a speed detector adapted to generate a signal proportional to the difference in speed between said counterweight and said image section, said counterweight and image section having the same speed when coupled for weight compensation;
a brake for braking the speed of said counterweight; and
a control circuit responsive to said signal for actuating said brake when the amplitude of said signal exceeds a predetermined value.

* * * * *